(12) United States Patent
Sison et al.

(10) Patent No.: US 11,389,330 B2
(45) Date of Patent: *Jul. 19, 2022

(54) MAGNETIC GOGGLE LENS CHANGING SYSTEM

(71) Applicant: Spy Optic Inc., Carlsbad, CA (US)

(72) Inventors: Brittany Sison, Carlsbad, CA (US); Christopher Frensley, Carlsbad, CA (US)

(73) Assignee: Spy Optic Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/776,936

(22) Filed: Jan. 30, 2020

(65) Prior Publication Data

US 2021/0196521 A1 Jul. 1, 2021

Related U.S. Application Data

(60) Provisional application No. 62/955,979, filed on Dec. 31, 2019.

(51) Int. Cl.
*A61F 9/02* (2006.01)

(52) U.S. Cl.
CPC ........ *A61F 9/025* (2013.01); *A61F 2210/009* (2013.01)

(58) Field of Classification Search
CPC .. A61F 9/025; A61F 9/02; A61F 9/028; A61F 9/027; A61F 9/029; A61F 2210/009
(Continued)

(56) References Cited

U.S. PATENT DOCUMENTS

| 2,526,737 A | 10/1950 | Farina |
| 3,056,140 A | 10/1962 | Lindblom |

(Continued)

FOREIGN PATENT DOCUMENTS

| CA | 2456476 A1 | 8/2004 |
| DE | 2063092 A1 | 7/1971 |

(Continued)

OTHER PUBLICATIONS

Patent Cooperation Treaty, International Search Report and Written Opinion for International Application No. PCT/US2020/067434, dated Feb. 17, 2021, 11 pages.

(Continued)

*Primary Examiner* — F Griffin Hall
(74) *Attorney, Agent, or Firm* — Stetina Brunda Garred and Brucker

(57) ABSTRACT

A goggle lens is configured for use with a goggle frame having a frame body and a pair of frame engagement members positioned at respective lateral end portions of the frame body. The goggle lens includes a lens rim, and a lens element that is transparent to allow a user to view through the lens element. A pair of lens engagement members are coupled to respective lateral end portions of the lens rim. The pair of lens engagement members are selectively engageable with respective ones of the pair of frame engagement members. The pair of lens engagement members include a locking lens engagement member comprising a first element coupled to the lens rim, and a second element moveably coupled to the first element for facilitating selective engagement and disengagement with the respective one of the pair of frame engagement members.

10 Claims, 4 Drawing Sheets

(58) Field of Classification Search
USPC .................. 2/439, 426, 441, 443, 436, 452
See application file for complete search history.

(56) References Cited

U.S. PATENT DOCUMENTS

| | | |
|---|---|---|
| 3,298,031 A | 1/1967 | Morgan |
| 3,363,262 A | 1/1968 | Lindblom |
| 3,377,626 A | 4/1968 | Smith |
| 3,395,406 A | 8/1968 | Smith |
| 3,505,680 A | 4/1970 | Ring |
| 3,533,686 A | 10/1970 | O'Shea |
| 3,754,298 A | 8/1973 | Menil |
| 3,783,452 A | 1/1974 | Benson et al. |
| 3,825,953 A | 7/1974 | Hunter |
| 3,896,496 A | 7/1975 | Leblanc |
| 3,924,271 A | 12/1975 | Hirschmann |
| 3,931,646 A | 1/1976 | Loughner |
| 3,945,044 A | 3/1976 | McGee et al. |
| 4,011,595 A | 3/1977 | Shields |
| 4,149,276 A | 4/1979 | Castro |
| 4,150,443 A | 4/1979 | McNeilly |
| 4,176,410 A | 12/1979 | Matthias |
| 4,264,987 A | 5/1981 | Runckel |
| 4,290,673 A | 9/1981 | Yamamoto |
| 4,317,240 A | 3/1982 | Angerman et al. |
| 4,425,669 A | 1/1984 | Grendol et al. |
| 4,428,081 A | 1/1984 | Smith |
| 4,443,893 A | 4/1984 | Yamamoto |
| 4,447,914 A | 5/1984 | Jannard |
| 4,455,689 A | 6/1984 | Boyer |
| 4,528,701 A | 7/1985 | Smith |
| 4,556,995 A | 12/1985 | Yamamoto |
| 4,571,748 A | 2/1986 | Carroll et al. |
| 4,603,442 A | 8/1986 | Barfield |
| 4,698,838 A | 10/1987 | Ishikawa et al. |
| 4,707,863 A | 11/1987 | McNeal |
| 4,716,601 A | 1/1988 | McNeal |
| 4,868,929 A | 9/1989 | Curcio |
| 4,918,753 A | 4/1990 | Mermillod |
| 4,977,627 A | 12/1990 | Metcalfe et al. |
| 4,989,274 A | 2/1991 | Patelski |
| 5,018,223 A | 5/1991 | Dawson et al. |
| 5,027,443 A | 7/1991 | Watkins |
| 5,046,200 A | 9/1991 | Feder |
| 5,056,163 A | 10/1991 | Chou |
| 5,069,541 A | 12/1991 | Holmes et al. |
| 5,093,940 A | 3/1992 | Nishiyama |
| 5,138,723 A | 8/1992 | Bolle |
| 5,182,817 A | 2/1993 | Branum |
| D334,758 S | 4/1993 | Reymondet et al. |
| 5,213,241 A | 5/1993 | Dewar et al. |
| 5,216,759 A | 6/1993 | Hewitt et al. |
| 5,339,119 A | 8/1994 | Gardner |
| 5,341,516 A | 8/1994 | Keim |
| D351,850 S | 10/1994 | Bolle |
| 5,363,512 A | 11/1994 | Grabos et al. |
| 5,371,555 A | 12/1994 | Nagel |
| 5,406,340 A | 4/1995 | Hoff |
| D358,159 S | 5/1995 | Lai |
| 5,410,763 A | 5/1995 | Bolle |
| 5,421,037 A | 6/1995 | Schulze |
| 5,423,092 A | 6/1995 | Kawai |
| 5,452,480 A | 9/1995 | Ryden |
| D364,181 S | 11/1995 | Arnette |
| 5,471,036 A | 11/1995 | Sperbeck |
| D367,664 S | 3/1996 | Simioni |
| 5,495,623 A | 3/1996 | Leonardi |
| 5,517,700 A | 5/1996 | Hoffman |
| D371,566 S | 7/1996 | Kolada et al. |
| 5,542,130 A | 8/1996 | Grabos et al. |
| 5,617,588 A | 4/1997 | Canavan et al. |
| 5,628,072 A | 5/1997 | Haslbeck et al. |
| 5,636,388 A | 6/1997 | Hodges |
| 5,642,530 A | 7/1997 | Parks |
| 5,650,866 A | 7/1997 | Haslbeck |
| 5,652,965 A | 8/1997 | Crooks |
| 5,655,228 A | 8/1997 | Chiang |
| 5,657,106 A | 8/1997 | Herald, Jr. et al. |
| 5,657,493 A | 8/1997 | Ferrero et al. |
| 5,685,022 A | 11/1997 | Essman et al. |
| 5,687,428 A | 11/1997 | Yamamoto |
| 5,689,834 A | 11/1997 | Wilson |
| 5,711,035 A | 1/1998 | Haslbeck |
| D390,248 S | 2/1998 | Pranger |
| D391,594 S | 3/1998 | Huh |
| 5,768,716 A | 6/1998 | Porsche |
| 5,802,622 A | 9/1998 | Baharad et al. |
| 5,809,580 A | 9/1998 | Arnette |
| 5,813,990 A | 9/1998 | Ryll |
| 5,815,235 A | 9/1998 | Runckel |
| 5,818,569 A | 10/1998 | Berent |
| 5,845,341 A | 12/1998 | Barthold et al. |
| D405,102 S | 2/1999 | Moritz et al. |
| 5,867,841 A | 2/1999 | Chiang |
| D408,431 S | 4/1999 | Simioni |
| 5,915,542 A | 6/1999 | Swiet |
| 5,927,281 A | 7/1999 | Monteleone et al. |
| 5,937,439 A | 8/1999 | Barthold et al. |
| 5,940,891 A | 8/1999 | Lane |
| D413,915 S | 9/1999 | Newcomb et al. |
| 5,966,745 A | 10/1999 | Schwartz et al. |
| 5,966,746 A | 10/1999 | Reedy et al. |
| 6,009,564 A | 1/2000 | Tackles et al. |
| 6,038,707 A | 3/2000 | Ryden et al. |
| 6,047,410 A | 4/2000 | Dondero |
| 6,049,917 A | 4/2000 | Ryden |
| 6,076,196 A | 6/2000 | Masumoto |
| D428,039 S | 7/2000 | Thixton |
| 6,092,243 A | 7/2000 | Wu et al. |
| 6,094,751 A | 8/2000 | Parks |
| 6,098,204 A | 8/2000 | Arnette |
| 6,098,205 A | 8/2000 | Schwartz et al. |
| 6,099,120 A | 8/2000 | De Lima |
| 6,105,177 A | 8/2000 | Paulson et al. |
| 6,119,276 A | 9/2000 | Newcomb et al. |
| 6,138,285 A | 10/2000 | Robrahn et al. |
| 6,138,286 A | 10/2000 | Robrahn et al. |
| D439,596 S | 3/2001 | Bolle |
| D442,206 S | 5/2001 | Meyerhoffer |
| 6,227,665 B1 | 5/2001 | Pernicka et al. |
| 6,253,387 B1 | 7/2001 | Yu |
| 6,282,727 B1 | 9/2001 | Lindahl |
| 6,282,728 B1 | 9/2001 | Baragar et al. |
| D450,833 S | 11/2001 | Olivieri |
| 6,321,391 B1 | 11/2001 | Basso |
| D457,545 S | 5/2002 | Khulusi |
| D457,551 S | 5/2002 | Khulusi |
| 6,415,452 B1 | 7/2002 | Watanabe et al. |
| 6,460,196 B2 | 10/2002 | Tsubooka et al. |
| 6,467,098 B1 | 10/2002 | Lee |
| D477,010 S | 7/2003 | Moritz et al. |
| 6,611,965 B1 | 9/2003 | Lee |
| 6,611,966 B1 | 9/2003 | Yamamoto et al. |
| 6,615,409 B2 | 9/2003 | Youmans et al. |
| 6,637,038 B1 | 10/2003 | Hussey |
| 6,665,885 B2 | 12/2003 | Masumoto |
| 6,691,324 B1 | 2/2004 | Nakamura |
| 6,704,944 B2 | 3/2004 | Kawainshi et al. |
| 6,715,157 B2 | 4/2004 | Mage |
| 6,718,561 B2 | 4/2004 | Dondero |
| 6,728,974 B2 | 5/2004 | Wadsworth |
| 6,732,382 B2 | 5/2004 | Dondero |
| 6,732,383 B2 | 5/2004 | Cleary et al. |
| 6,772,448 B1 | 8/2004 | Hockaday et al. |
| 6,826,785 B2 | 12/2004 | McNeal |
| D505,444 S | 5/2005 | Borlet et al. |
| 6,896,366 B2 | 5/2005 | Rice et al. |
| D509,236 S | 9/2005 | Sheldon |
| 6,952,841 B2 | 10/2005 | Schary et al. |
| 6,964,067 B1 | 11/2005 | Hartman |
| 6,986,169 B2 | 1/2006 | Nakamura |
| 7,039,959 B2 | 5/2006 | Dondero |
| 7,052,127 B2 | 5/2006 | Harrison |
| 7,058,992 B1 | 6/2006 | Ogonowsky |

(56) References Cited

U.S. PATENT DOCUMENTS

| | | |
|---|---|---|
| 7,062,797 B2 | 6/2006 | Khulusi |
| 7,073,208 B2 | 7/2006 | Penque, Jr. et al. |
| 7,096,514 B2 | 8/2006 | Khulusi |
| 7,100,215 B2 | 9/2006 | Shiue |
| 7,137,153 B2 | 11/2006 | Hussey |
| D537,098 S | 2/2007 | Sheldon et al. |
| 7,181,779 B2 | 2/2007 | Hussey |
| 7,192,137 B2 | 3/2007 | Ishibashi et al. |
| 7,200,875 B2 | 4/2007 | Dondero |
| D542,327 S | 5/2007 | Hsu |
| D542,829 S | 5/2007 | Hsu |
| D542,830 S | 5/2007 | Hsu |
| 7,260,850 B2 | 8/2007 | Ambuske et al. |
| D550,749 S | 9/2007 | Chiang |
| D552,662 S | 10/2007 | Woxing |
| 7,290,294 B2 | 11/2007 | Kita |
| D559,299 S | 1/2008 | Tabacchi |
| 7,343,631 B2 | 3/2008 | Lin |
| 7,356,854 B2 | 4/2008 | Sheldon |
| 7,370,374 B2 | 5/2008 | Penque, Jr. et al. |
| 7,404,217 B2 | 7/2008 | Polinelli et al. |
| 7,407,283 B2 | 8/2008 | Babineau et al. |
| 7,510,279 B2 | 3/2009 | Van Atta et al. |
| D591,786 S | 5/2009 | Wang |
| 7,526,813 B2 | 5/2009 | Tominaga et al. |
| D598,040 S | 8/2009 | Sheldon et al. |
| D616,915 S | 6/2010 | Silveria et al. |
| D626,166 S | 10/2010 | Yang |
| D626,582 S | 11/2010 | Cheng |
| D640,724 S | 6/2011 | Goodman et al. |
| D649,178 S | 11/2011 | Moritz et al. |
| D649,577 S | 11/2011 | Goodman et al. |
| 8,166,578 B2 | 5/2012 | Tan |
| D669,113 S | 10/2012 | Sandor et al. |
| D675,244 S | 1/2013 | Orzeck et al. |
| D685,839 S | 7/2013 | Pearson et al. |
| D687,479 S | 8/2013 | Moritz et al. |
| D687,881 S | 8/2013 | Ginther et al. |
| D688,296 S | 8/2013 | Pearson et al. |
| D695,335 S | 12/2013 | Goodman et al. |
| 8,893,314 B2 | 11/2014 | Chen et al. |
| 9,720,255 B2 | 8/2017 | Park |
| 9,895,266 B2 | 2/2018 | Reynolds et al. |
| 10,159,603 B2 | 12/2018 | Rees et al. |
| 11,103,383 B2 * | 8/2021 | Sison ............... A61F 9/025 |
| 2002/0029408 A1 | 3/2002 | Lindahl |
| 2002/0148034 A1 | 10/2002 | Lee |
| 2002/0157175 A1 | 10/2002 | Dondero |
| 2003/0110552 A1 | 6/2003 | Youmans et al. |
| 2005/0015862 A1 | 1/2005 | Dondero |
| 2005/0128426 A1 | 6/2005 | Shiue |
| 2006/0048289 A1 | 3/2006 | Shiue |
| 2006/0191062 A1 | 8/2006 | Matera |
| 2006/0272078 A1 * | 12/2006 | Polinelli ............... A61F 9/029 2/436 |
| 2007/0033718 A1 | 2/2007 | Lin |
| 2008/0109949 A1 | 5/2008 | Kinsella |
| 2009/0019620 A1 | 1/2009 | Reed |
| 2009/0038059 A1 | 2/2009 | McNeal et al. |
| 2009/0122258 A1 | 5/2009 | Fielding, Jr. |
| 2010/0229292 A1 | 9/2010 | Tan |
| 2012/0038879 A1 | 2/2012 | Reyes et al. |
| 2013/0185849 A1 | 7/2013 | Laughlin et al. |
| 2014/0033408 A1 * | 2/2014 | Currens ............... A61F 9/025 2/431 |
| 2014/0157496 A1 | 6/2014 | Ginther et al. |
| 2014/0189943 A1 | 7/2014 | Tobia |
| 2015/0049294 A1 | 2/2015 | Chin |
| 2015/0124211 A1 | 5/2015 | Park |
| 2015/0143619 A1 | 5/2015 | Cross |
| 2015/0238361 A1 | 8/2015 | McCulloch et al. |
| 2018/0168865 A1 * | 6/2018 | Hilton ............... A61F 9/025 |
| 2019/0113773 A1 * | 4/2019 | Langenwalter ......... G02C 3/003 |

FOREIGN PATENT DOCUMENTS

| | | |
|---|---|---|
| DE | 2943472 A1 | 5/1981 |
| EP | 504518 A1 | 9/1992 |
| EP | 1095577 A2 | 5/2001 |
| JP | 956741 | 3/1997 |
| JP | 2016131832 A | 7/2016 |
| WO | 2009101645 A1 | 8/2009 |

OTHER PUBLICATIONS

PCT Search Report and Written Opinion for PCT/US18/43916 (dated Oct. 4, 2018).

PCT Search Report and Written Opinion for PCT/US15/55763 (dated Jan. 12, 2016).

* cited by examiner

MAGNETIC GOGGLE LENS CHANGING SYSTEM

CROSS-REFERENCE TO RELATED APPLICATIONS

This application relates to and claims the benefit of U.S. Provisional Application No. 62/955,979 filed Dec. 31, 2019 and entitled "MAGNETIC GOGGLE LENS CHANGING SYSTEM," the entire contents of which is hereby wholly incorporated by reference.

STATEMENT RE: FEDERALLY SPONSORED RESEARCH/DEVELOPMENT

Not Applicable

BACKGROUND

1. Technical Field

The present disclosure relates generally to a goggle, and more particularly, the present disclosure relates to a goggle having a goggle lens sized and configured to be detachably connectable to a goggle frame in an easy and rapid fashion.

2. Description of the Related Art

In order to protect one's eyes during many sports or outdoor activities such as snowboarding, skiing, skydiving, paragliding, and so on, a person may wear goggles. Typically, goggles are constructed of a frame, lenses which are fixedly mounted on the forward face of the frame, padding for comfort and absorbing sweat which is attached to the rear face of the frame, and a band for fixing the goggles to a user's head. The goggles may be positioned over the user's eyes, such that the user looks through the lens, with the band extending around the user's head.

While generally all goggles share this basic design, it has been found that the experience of wearing goggles during certain sports or outdoor activities may be enhanced by wearing specialized or preferred lenses for that sport or activity. For example, variation in the colors of lenses may affect a wearer's perception of the brightness and contrast of their environment, as well as a wearer's depth perception and ability to perceive certain colors. Furthermore, the lens may be colored or have other attributes which enhance the overall aesthetic appeal of the goggle.

Lenses which are fixed to the goggle frame may limit the overall use of the goggle. For instance, the functional attributes of a given lens may be adapted for use in certain environmental conditions. For instance, darkly tinted lenses may be useful in very bright conditions, but not useful in darker conditions. Conversely, lightly tinted lenses may be useful in darker conditions, and not as useful in lighter conditions. Furthermore, the aesthetic attributes of a given lens may fall out of favor with a user as that user's aesthetic appeal changes. Additionally, during certain sports or outdoor activities, it is common that the lenses on a pair of goggles may become damaged, such as by becoming cracked, scratched, or crazed.

Thus, a wearer who owns a pair of conventional goggles with integrated lenses, but desires to wear different lenses on their goggles, or to replace damaged lenses on their goggles, may be required to purchase and adjust to an entirely new pair of goggles, or take the goggles to the manufacturer or a specialist for replacement of lenses.

Accordingly, there is a need in the art for a goggle lens which can accommodate quick and easy engagement with a corresponding goggle frame. Various aspects of the present disclosure address this particular need, as will be discussed in more detail below.

BRIEF SUMMARY

Various aspects of the present disclosure are directed toward a goggle for use in snow sports (e.g., snowboarding, snow skiing, etc.), which may include detachable lens. The lens may be detachably connected to a goggle frame via a magnetic connection, as well as through a mechanical slide lock mechanism. The magnetic connection may allow the lens to be easily registered or aligned relative to the goggle frame, while the slide lock mechanism may provide a more secure attachment between the goggle frame and the lens. The combination of the magnetic attachment and mechanical attachment may allow for attachment or detachment of the lens relative to the goggle frame while a user is wearing gloves, as is often the case when participating in snow sports.

In accordance with one embodiment of the present disclosure, there is provided a goggle comprising a goggle frame extending around a goggle frame opening. At least one magnetically attractable frame connector coupled to the goggle frame. A lens is positionable adjacent the goggle frame, with the lens being sized and configured to extend over the goggle frame opening when the lens is positioned adjacent the goggle frame opening. At least one magnetically attractable lens connector is coupled to the lens and magnetically connectable to the at least one frame connector to magnetically connect the lens to the goggle frame. A pair of attachment bodies are connected to the lens. A pair of locking tabs are slidably connected to the goggle frame, with each locking tab being transitional between an unlocked position and a locked position and engaging a respective one of the pair of attachment bodies when the locking tab is moved from the unlocked position to the locked position.

The lens connector may be a magnet. The lens connector may be a metallic material. The frame connector may be a magnet. The frame connector may be a metallic material.

The frame may include a pair of channels, with each locking tab being translatable within a respective one of the pair channels. Each locking tab may include a finger gripping body and a locking body, with the finger gripping body extending outside of the goggle frame opening, and the locking body extending within the goggle frame opening. Each locking body may include a U-shaped recess. Each attachment body may include a ramp at least partially defining an attachment body channel, and each attachment body may be received in the U-shaped recess of a respective one of the pair of locking tabs. Each locking tab may be received in the attachment body channel when the lens connector is magnetically coupled to the goggle frame connector and the locking tab is moved to the locked position.

Each attachment body may include a shaft and a head, with the shaft being positioned between the head and the lens. Each shaft may include a first edge extending from the head and a second edge extending from the first edge, with the first and second edges defining an angle greater than 90 degrees.

The lens may include a convex outer surface and an opposing concave inner surface. Each attachment body may extend away from the concave inner surface.

According to another embodiment, there is provided a lens assembly for use with a goggle frame defining a goggle frame opening and having at least one magnetically attractable frame connector coupled to the goggle frame and a pair of locking tabs slidably connected to the goggle frame. The lens assembly includes a lens positionable adjacent the goggle frame. The lens is sized and configured to extend over the goggle frame opening when the lens is positioned adjacent the goggle frame opening. The lens assembly additionally includes at least one magnetically attractable lens connector coupled to the lens and magnetically connectable to the at least one frame connector to magnetically connect the lens to the goggle frame. A pair of attachment bodies are connected to the lens. Each attachment body is engageable with a respective one of the locking tabs for mechanically connecting the lens to the frame.

According to another embodiment, there is provided a goggle frame assembly for use with a lens, at least one magnetically attractable lens connector coupled to the lens, and a pair of attachment bodies connected to the lens. The goggle frame assembly includes a goggle frame extending around a goggle frame opening sized to be complementary to the lens. At least one magnetically attractable frame connector is coupled to the goggle frame and is magnetically connectable to the at least one magnetically attractable lens connector. A pair of locking tabs are slidably connected to the goggle frame. Each locking tab is transitional between an unlocked position and a locked position and engages a respective one of the pair of attachment bodies when the lens is positioned adjacent the goggle frame and the locking tab is moved from the unlocked position to the locked position.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

Figure 1:
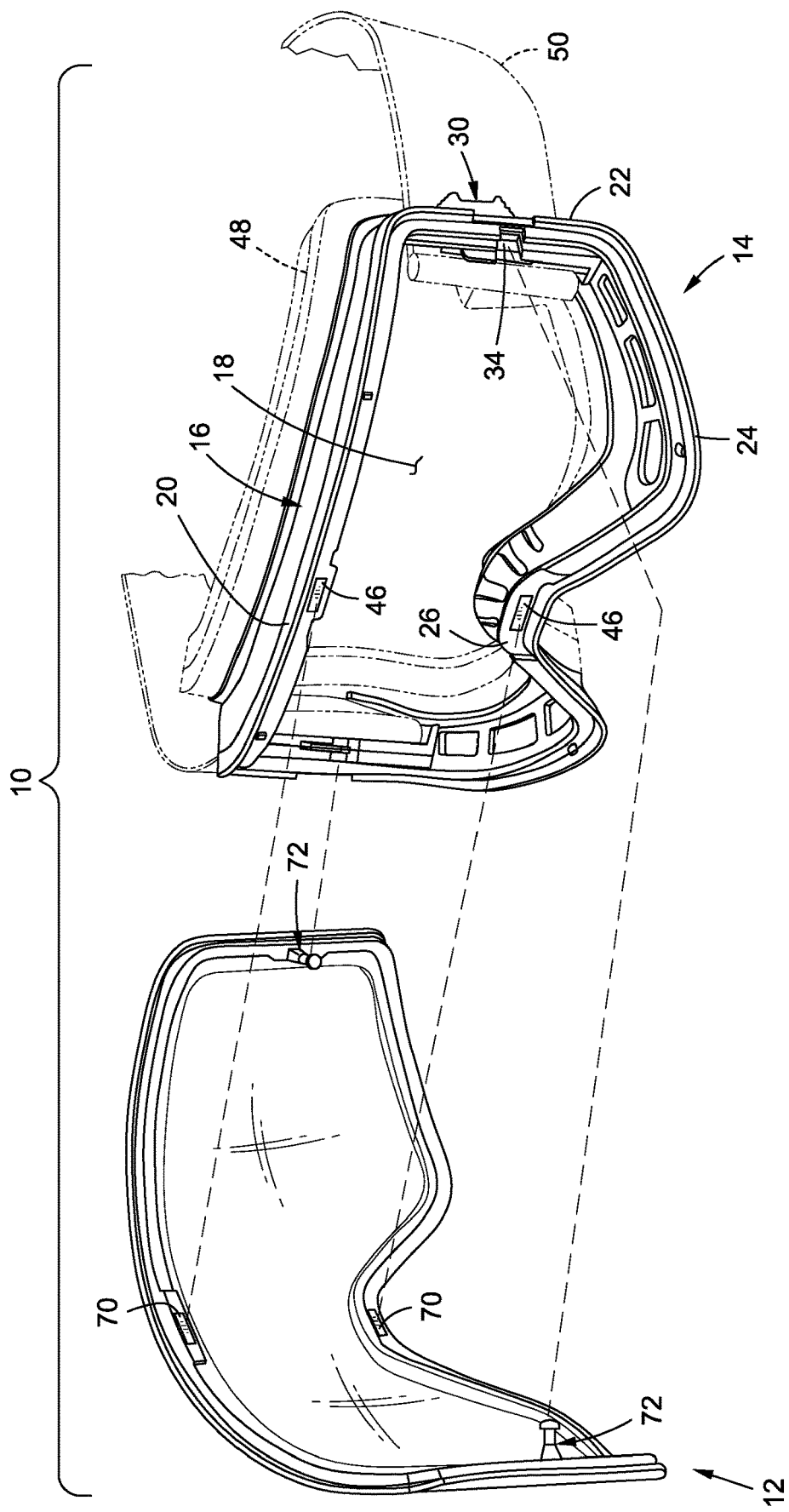
FIG. 1 is an upper perspective view of a goggle having a lens detached from a goggle frame.

The detailed description set forth below in connection with the appended drawings is intended as a description of certain embodiments of a magnetic goggle lens assembly and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Referring now to the drawings, wherein the showings are for purposes of illustrating a preferred embodiment of the present disclosure, and are not for purposes of limiting the same, there is depicted a goggle 10 having a goggle lens assembly 12 specifically configured and adapted to be detachably engageable with a goggle frame assembly 14. The goggle lens assembly 12 may be engageable with the goggle frame assembly 14 via magnetic attraction as well as mechanical interconnection. The magnetic attraction may register or align the lens assembly 12 relative to the goggle frame assembly 14, while also providing an audible and tactile feel to the user when the lens assembly 12 becomes magnetically engaged to the goggle frame assembly 14. The mechanical interconnection may provide for a more secure attachment between the lens assembly 12 and the goggle frame assembly 14. Furthermore, the configuration of the lens assembly 12 and the goggle frame assembly 14 may allow for attachment or detachment of the lens assembly 12 relative to the goggle frame assembly 14 while the user is wearing gloves, as may often be the case during use of the goggle 10 while participating in snow sports.

The ability to quickly and easily detach the goggle lens assembly 12 from the goggle frame assembly 14 allows a user to utilize a goggle lens assembly 12 that is suitable for the expected environmental conditions. For instance, a dark goggle lens may be used in bright conditions, and alternatively, a lightly tinted lens may be used in dark lighting conditions. Furthermore, one goggle lens assembly 12 may be interchanged with another goggle lens assembly 12 to give the overall goggle 10 a different appearance or look. As such, interchangeable goggle lenses enhance the overall commercial appeal of the goggle assembly 10. Furthermore, interchangeable lenses allow a user to replace a broken lens assembly 12 with a new lens assembly 12, and thus, the user is not required to purchase an entirely new goggle 10.

According to one embodiment, the goggle frame assembly 14 includes a main body 16 which circumnavigates a central frame opening 18 and defines a curvature which allows the goggle frame assembly 14 to comfortably fit on a user's face. The main body 16 may include an upper portion 20 extending between a pair of lateral portions 22, and a lower portion 24 having a centrally located bridge section 26 adapted to extend over a user's nose. At least a portion of the main body 16 may be formed from a flexible material to enhance the fit and comfort of the goggle 10 when worn by the wearer. Exemplary flexible materials include plastic (e.g., polyurethane), rubber, or other materials known in the art.

According to one embodiment, the main body 16 includes a pair of channels 28 formed therein, which accommodate a corresponding pair of locking tabs 30 slidably connected to the main body 16 via the channels 28. Each channel 28 may be located in a respective lateral portion 22. According to one embodiment, each lateral portion 22 includes a pair of plates 32 that are connected to each other and which collectively define the channel 28. Each pair of plates 32 may include projections, contours, recesses, etc., which may interface with the locking tabs 30 and may be associated with various positions of the locking tab 30 relative to the main body 16. For instance, the positions of the locking tab 30 may include an unlocked position, a locked position, and an intermediate position, as will be described in more detail below.

The main body 16 may further include a pair of engagement slots 34 formed in the main body 16 and in communication with respective channels 28. The engagement slots 34 are configured to receive attachment bodies included on the lens assembly 12 for securing the lens assembly 12 to the goggle frame assembly 14, as will be described in more detail below. Each engagement slot 34 extends from a forward surface of the main body 16 and into the main body 16 toward the respective channel. In one embodiment, the engagement slot 34 may extend generally perpendicularly to the corresponding channel.

As noted above, the goggle frame assembly 14 may include a pair of locking tabs 30 coupled to the main body 16. Each locking tab 30 may be translatable within a respective channel 28 between an unlocked position and a locked position. In the unlocked position, the locking tab 30 is positioned to allow the lens assembly 12 to be attached or removed from the main body 16. In this regard, when the locking tab 30 is in the unlocked position, the locking tab 30 does not inhibit mechanical attachment or detachment of the lens assembly 12 relative to the goggle frame assembly 14. In the locked position, the locking tab 30 is positioned to engage with a portion of the lens assembly 12 to secure the lens assembly 12 to the main body 16, as will be described in more detail below.

According to one embodiment, each locking tab 30 includes a finger gripping body 36 and a locking body 38. The finger gripping body 36 is configured to extend outside of the central frame opening 18 and is sized to provide a structure which a user may apply a force with a finger. In this regard, the finger gripping body 36 may include a series of ridges 40 to enhance engagement with the user's finger. Given that various embodiments of the goggle 10 may be used when participating in snow sports or other activities where a user may be wearing a glove, the finger gripping body 36 may be particularly sized and configured to allow a user to engage with the finger gripping body 36 while wearing a glove and transition the finger gripping body 36 between the unlocked and locking positions.

Each locking tab 30 may additionally include a locking body 38 extending within a respective channel in the main body 16. In this regard, while the finger gripping body 36 is configured to be exposed on the outside of the main body 16, the locking tab 30 may be generally concealed by residing in the channel 28. Each locking body 38 may include a U-shaped recess 42 which engages a portion of the lens assembly 12 when the lens assembly 12 is engaged with the goggle frame assembly 14. The locking body 38 may additionally include one or more projections 44 which may interface with structural elements on the main body 16 to provide frictional stops as the locking tab 30 moves relative to the main body 16.

The goggle 10 may additionally include at least one magnetically attractable frame connector 46 coupled to the main body 16. In the exemplary embodiment, the goggle 10 includes a pair of frame connectors 46, with one frame connector 46 being coupled to the main body 16 a central region of the upper portion 20, and another frame connector 46 may be coupled to a middle region of the bridge section 26. The frame connectors 46 may be aligned along a generally central axis. It is contemplated that additional frame connectors 46 may be coupled to the main body 16 at other locations thereof. The frame connector 46 may be a magnet, or alternatively, the frame connector 46 may be formed from a non-magnetic metallic material that is magnetically attractable to a magnet.

The goggle frame assembly 14 may additionally include a compressible liner 48 may extend over an inner surface of the main body 16 (i.e., that portion of the main body 16 facing the user during use) and may be positioned to interface with the user when the goggle 10 is worn. The compressible liner 48 may be formed from foam or other materials known in the art, and may be sized and positioned to form a barrier between the main body 16 and the user to prevent precipitation, ice, mud, or other debris from entering the space between the goggle 10 and the user. An elastic strap 50 may be connected to the main body 16 at the lateral portions 22 thereof, with the strap 50 being adapted to extend around the user's head for securing the goggle 10 to the user.

Figure 2:
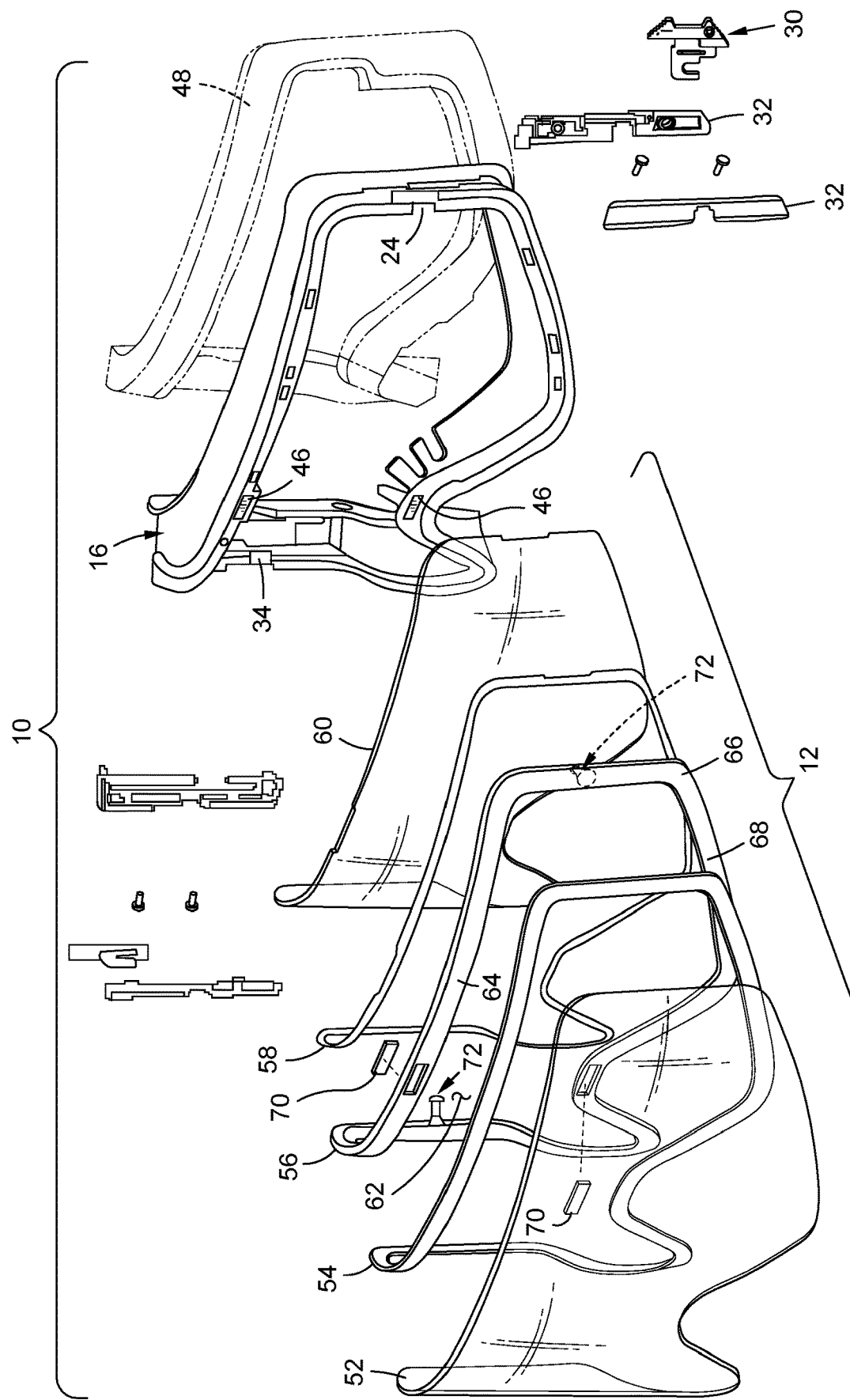
FIG. 2 is an upper perspective view of the goggle frame and lens assembly
Figure 4:
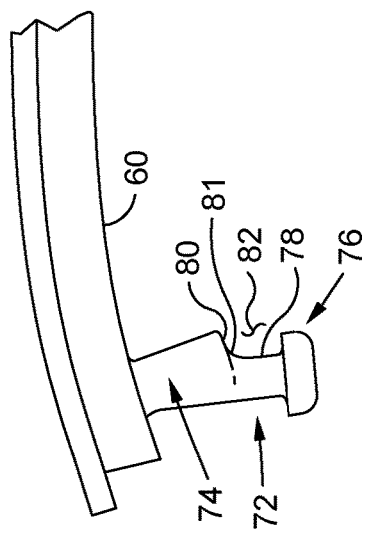
FIG. 4 is a top view of the locking tab.

Referring now to FIG. 2, the goggle lens assembly 12 generally includes an outer lens 52, an outer adhesive 54, a lens frame 56, an inner adhesive 58, and an inner lens 60. According to one embodiment, the lens frame 56 defines a lens opening 62, with the lens frame 56 circumnavigating the lens opening 62. The lens opening 62 is substantially similar in size and shape to the central frame opening 18 defined by the main body 16, such that when the goggle lens 12 is attached to the main body 16, the lens opening 62 is aligned with the central frame opening 18 to allow the user to look through the goggle 10. The lens frame 56 includes an upper portion 64, a pair of lateral portions 66, and a lower portion 68 having a bridge section shaped to extend over a user's nose during use. The lens frame 56 provides a structure upon which the outer lens 52 and inner lens 60 may be secured.

The outer adhesive 54 is used to secure the outer lens 52 to the lens frame 56, and inner adhesive 58 is used to secure the inner lens 60 to the lens frame 56. According to one embodiment, the outer lens 52 and inner lens 60 are coupled to opposing surfaces of the lens frame 56. Both the outer lens 52 and inner lens 60 may be transparent bodies adapted to allow the user to view therethrough. As used herein, the term "transparent" simply refers to the ability of a user to at least partially look through the lens 52, 60. In this regard, it is understood that although the outer lens 52 and inner lens 60 are transparent, one or both of the outer lens 52 and the inner lens 60 may have tint, polarization, film, or other aesthetic enhancements (e.g., color, reflectance, etc.) or functional enhancements (e.g., reducing glare) made thereto. The tint, polarization, or color enhancements may be functional in nature, such as reducing glare or brightness, or may be intended to enhance the overall aesthetic appeal of the goggle 10. The outer lens 52 and inner lens 60 may be formed of polycarbonate, TRIVEX, or other lens materials known in the art.

Although the exemplary embodiment shows the goggle lens 12 as having the outer lens 52 and the separate inner lens 60, it is understood that other embodiments may only include a single lens, such as the outer lens 52.

The goggle lens assembly 12 may additionally include one or more magnetic lens connectors 70 and one or more attachment bodies 72 to facilitate magnetic and mechanical connection to the main body 16. The exemplary lens assembly 12 includes a pair of magnetic lens connectors 70 coupled thereto. The magnetic lens connectors 70 are sized and configured to magnetically connect with the magnetic frame connectors 46 located on the main body 16. In this regard, one magnetic lens connector 70 being attached to a top portion of the lens frame 56 and may be magnetically connectable to the magnetic frame connector 46 located on the top of the main body 16. Another magnetic lens connector 70 may be attached to a bridge portion of the lens frame 56 and may be magnetically connectable to the magnetic frame connector 46 located on the bridge portion of the main body 16. The lens connectors 70 may be aligned along a generally central axis. It is contemplated that additional lens connectors 70 may be coupled to the lens frame 56 at other locations thereof. The lens connector 70 may be a magnet, or alternatively, the lens connector 70 may be formed from a non-magnetic metallic material that is magnetically attractable to a magnet. In this regard, in one embodiment, both the lens connector 70 and the frame connector 46 may be magnets, while in another embodiment, the lens connector 70 is a magnet, while the frame connector 46 is not a magnet, and is simply a metallic material that is magnetically attractable to the lens connector. In yet another embodiment, the frame connector 46 is a magnet, while the lens connector 70 is not a magnet, and is simply a metallic material that is magnetically attractable to the frame connector.

Figure 7:
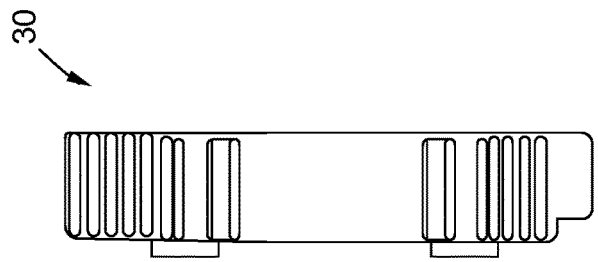
FIG. 7 is a top view of an attachment body coupled to the lens and configured to be engageable with the locking tab.
Figure 3:
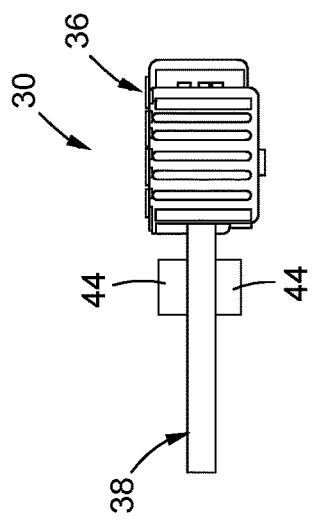
FIG. 3 is an upper perspective view of a locking tab used for connecting the lens to the goggle frame.
Figure 5:
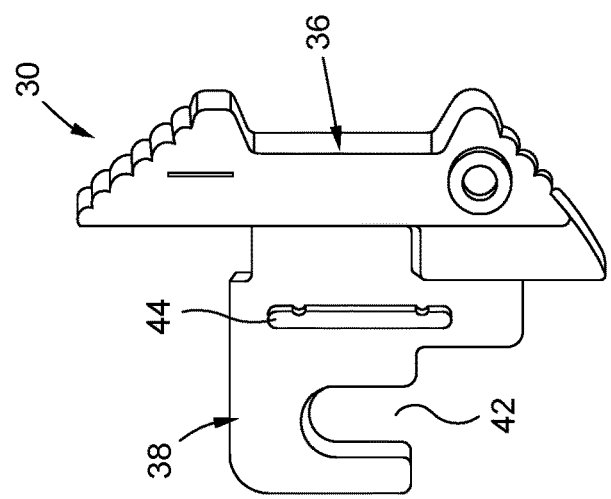
FIG. 5 is a front view of the locking tab.
Figure 6:
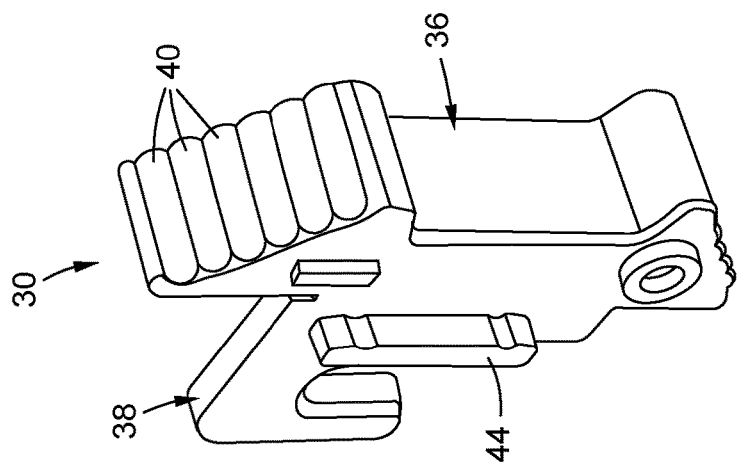
FIG. 6 is an end view of the locking tab

The exemplary lens assembly 12 further includes a pair of attachment bodies 72 coupled to the lens frame 56. Each attachment body 72 may include a shaft 74 and a head 76, with the shaft 74 being positioned between the head 76 and the inner lens 60. As is apparent from FIG. 7, the head 76 may be in a distal position relative to the shaft 74, and thus, may be referred to as a distal head. Furthermore, the head 76 may be enlarged relative to at least a portion of the shaft 74. Each shaft 74 may include a first edge 78 extending from the head 76 and a second edge 80 extending from the first edge 78, with the first and second edges 78, 80 defining an angle greater than 90 degrees.

Each attachment body 72 may include a ramp defined by the second edge 78 at least partially defining an attachment body channel 82, and each attachment body 72 may be received in the U-shaped recess 42 of a respective one of the pair of locking tabs 30. Each locking tab 30 may be received in the attachment body channel 82 when the lens connector 70 is magnetically coupled to the goggle frame connector 46 and the locking tab 30 is moved to the locked position.

Figure 10:
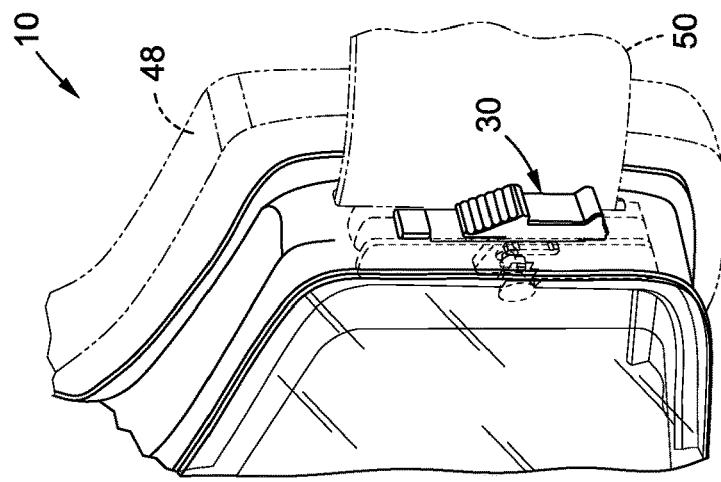
FIGS. 8-10 are upper perspective views depicting a sequence of attaching the lens to the goggle frame.
Figure 9:
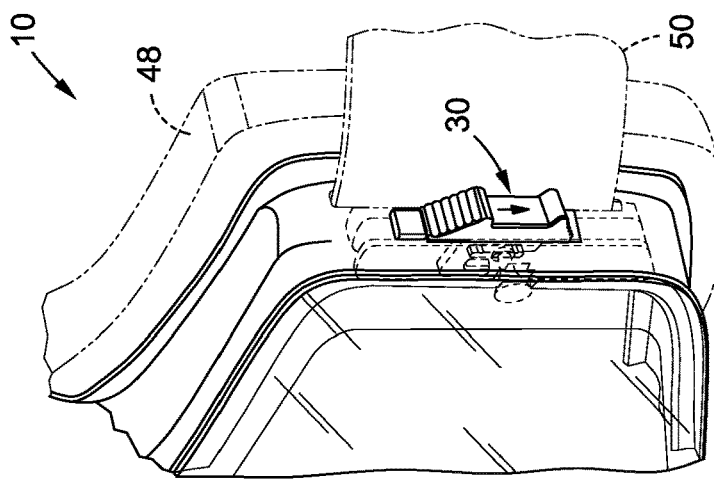
Figure 8:
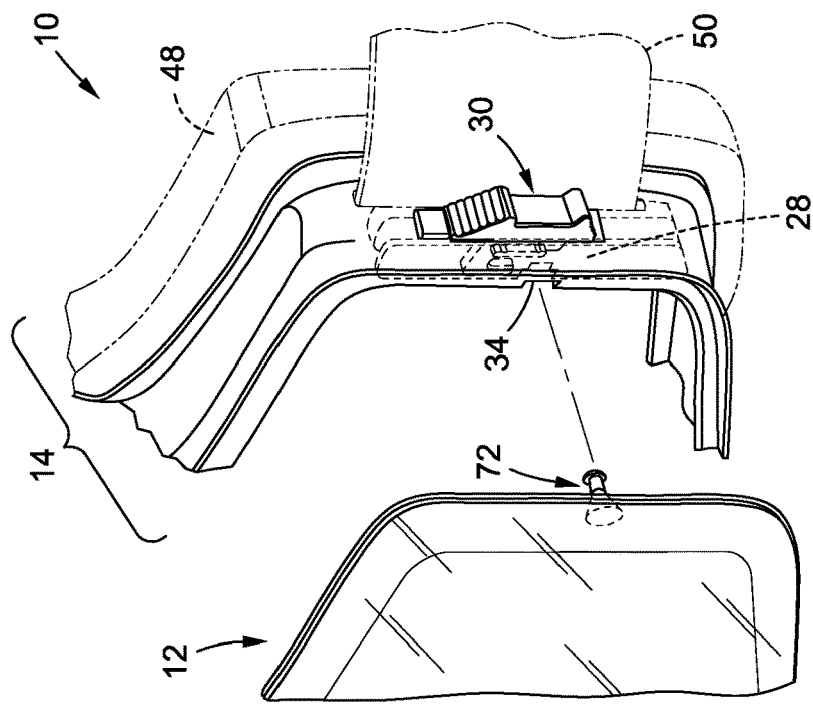

With the basic structural features of the goggle 10 described above, and with reference specifically to FIGS. 8-10, a discussion of an exemplary use of the goggle 10 will now be provided. A user may have several goggle lenses 12 available for use with a goggle frame assembly 14. When a user selects a particular goggle lens 12, the user aligns the goggle lens 12 with the goggle frame assembly 14 and ensures the locking tabs 30 on the frame assembly 14 are in their respective unlocked positions. In particular, the goggle lens 12 is positioned with the inner lens 60 facing toward the goggle frame assembly 14, and the outer lens 52 facing away from the goggle frame assembly 14. Furthermore, the magnetic lens connectors 70 are aligned with the corresponding magnetic frame connectors, and the lens attachment bodies 72 are aligned with respective engagement slots 34 on the main body 16.

The lens assembly 12 is moved closer to the main body 16 until the magnetic attraction between the magnetic lens connectors 70 and the magnetic frame connectors 46 is sufficient to independently couple the lens assembly 12 to the frame assembly 14. In this regard, the magnetic attraction between the magnetic lens connectors 70 and magnetic frame connectors 46 may allow the lens assembly 12 to be properly aligned and registered relative to the frame assembly 14, with the attachment bodies 72 of the lens assembly 12 received within the respective engagement slots 34 on the main body 16.

The locking tabs 30 are then moved from their respective unlocked configurations toward their locked configurations. More specifically, each locking tab 30 translates relative to the main body 16, and the locking body 38 on the locking tab 30 engages the ramp on the attachment body 72. As the locking tab 30 continues toward the locked position, the locking body 38 moves along the ramp until the locking body 38 is received in the attachment body channel 82 of the attachment body 72, and the attachment body 72 is received in the U-shaped recess 42 of the locking body 38. When the locking tabs 30 are in their respective locked positions, the lens assembly 12 is securely fastened to the goggle frame assembly 14. In particular, the lens assembly 12 is coupled to the goggle frame assembly 14 through magnetic attraction via the magnetic lens connector 70 and frame connector 46, as well as being connected through mechanical engagement between the locking tabs 30 and the attachment bodies 72.

To release the lens assembly 12 from the main body 16, the locking tabs 30 are moved from their locked positions toward their unlocked positions by translating relative to the main body 16. As the locking tabs 30 translate, the locking body 38 is moved out of the attachment body channel 82 to disengage the locking body 38 of the locking tab 30 from the corresponding attachment body 72. In this regard, the mechanical interconnection between the lens assembly 12 and the goggle frame assembly 14 is disconnected. However, the magnetic attraction may remain. Thus, the user may pull the lens assembly 12 away from the main body 16 with sufficient force to overcome the magnetic attraction between the lens assembly 12 and the goggle frame assembly 14.

The detachable engagement between the lens assembly 12 and the goggle frame assembly 14 may allow a user to quickly and easily swap one goggle lens 12 for another goggle lens 12. The lenses may be swapped for functional reasons, such as to attach a lens having a preferred tint, or replace a broken lens; or the lenses may be swapped for aesthetic reasons. As such, the ability to easily interchange one lens for another results in a highly versatile goggle 10. Furthermore, the use of the magnetic attraction and the mechanical interconnection achieved via the locking tabs 30 may allow a user to attach or detach the lens assembly 12 relative to the main body 16 while the user wears gloves.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A goggle comprising:
   a goggle frame extending around a goggle frame opening;
   at least one magnetically attractable frame connector coupled to the goggle frame;
   a lens positionable adjacent the goggle frame, the lens being sized and configured to extend over the goggle frame opening when the lens is positioned adjacent the goggle frame opening;
   at least one magnetically attractable lens connector coupled to the lens and magnetically connectable to the at least one frame connector to magnetically connect the lens to the goggle frame;
a pair of attachment bodies connected to the lens; and
a pair of locking tabs slidably connected to the goggle frame, each locking tab being transitional between an unlocked position and a locked position and engaging a respective one of the pair of attachment bodies when the locking tab is moved from the unlocked position to the locked position;
wherein the goggle frame includes a pair of channels, each locking tab being translatable within a respective one of the pair channels; and
wherein each locking tab includes a finger gripping body and a locking body, the finger gripping body extending outside of the goggle frame opening and being configured to translate along an outer surface of the goggle frame, and the locking body extending within the goggle frame opening.

2. The goggle recited in claim 1, wherein the lens connector is a magnet.

3. The goggle recited in claim 1, wherein the lens connector is a metallic material.

4. The goggle recited in claim 1, wherein the frame connector is a magnet.

5. The goggle recited in claim 1, wherein the frame connector is a metallic material.

6. The goggle recited in claim 1, wherein each locking body includes a U-shaped recess.

7. The goggle recited in claim 6, wherein each attachment body includes a ramp at least partially defining an attachment body channel, each attachment body being received in the U-shaped recess of a respective one of the pair of locking tabs, and each locking tab being received in the attachment body channel when the lens connector is magnetically coupled to the goggle frame connector and the locking tab is moved to the locked position.

8. The goggle recited in claim 1, wherein each attachment body includes a shaft and a head, the shaft being positioned between the head and the lens, each shaft having a first edge extending from the head and a second edge extending from the first edge, the first and second edges defining an angle greater than 90 degrees.

9. The goggle recited in claim 1, wherein the lens includes a convex outer surface and an opposing concave inner surface, each attachment body extending away from the concave inner surface.

10. A goggle frame assembly for use with a lens, at least one magnetically attractable lens connector coupled to the lens, and a pair of attachment bodies connected to the lens, the goggle frame assembly comprising:
a main body extending around a goggle frame opening sized to be complementary to the lens;
at least one magnetically attractable frame connector coupled to the goggle frame and magnetically connectable to the at least one magnetically attractable lens connector; and
a pair of locking tabs slidably connected to the goggle frame, each locking tab being transitional between an unlocked position and a locked position and engaging a respective one of the pair of attachment bodies when the lens is positioned adjacent the goggle frame and the locking tab is moved from the unlocked position to the locked position;
wherein the frame includes a pair of channels, each locking tab being translatable within a respective one of the pair channels; and
wherein each locking tab includes a finger gripping body and a locking body, the finger gripping body extending outside of the goggle frame opening, and the locking body extending within the goggle frame opening.

* * * * *